United States Patent
Park et al.

(10) Patent No.: US 8,173,356 B2
(45) Date of Patent: May 8, 2012

(54) THREE DIMENSIONAL SCAFFOLD AND METHOD OF FABRICATING THE SAME

(75) Inventors: Chin Sung Park, Yongin-si (KR); Joon Ho Kim, Seongnam-si (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 1658 days.

(21) Appl. No.: 11/509,368

(22) Filed: Aug. 24, 2006

(65) Prior Publication Data

US 2007/0048964 A1 Mar. 1, 2007

(30) Foreign Application Priority Data

Aug. 24, 2005 (KR) ........................ 10-2005-0077847

(51) Int. Cl.
*G03F 7/00* (2006.01)
*G03F 7/004* (2006.01)
*G03F 7/26* (2006.01)
*G03F 7/40* (2006.01)

(52) U.S. Cl. ..................... 430/312; 430/270.1; 430/311; 430/330; 430/331

(58) Field of Classification Search ............... 430/270.1, 430/311, 312, 330, 331
See application file for complete search history.

(56) References Cited

U.S. PATENT DOCUMENTS

| | | | |
|---|---|---|---|
| 6,645,432 B1 | 11/2003 | Anderson et al. | |
| 6,652,244 B2 * | 11/2003 | Ihring et al. | 417/273 |
| 7,012,291 B2 * | 3/2006 | Behfar et al. | 257/290 |
| 7,229,745 B2 * | 6/2007 | Lamarre | 430/313 |
| 7,550,385 B2 * | 6/2009 | Lavoie et al. | 438/681 |
| 7,790,357 B2 * | 9/2010 | Jung | 430/311 |
| 7,820,358 B2 * | 10/2010 | Woerz et al. | 430/270.1 |
| 7,897,058 B2 * | 3/2011 | Van Haren et al. | 216/41 |
| 2003/0215733 A1 * | 11/2003 | Cheng et al. | 430/137.14 |
| 2007/0042287 A1 * | 2/2007 | Lin | 430/246 |
| 2009/0233240 A1 * | 9/2009 | Baik et al. | 430/312 |
| 2010/0112463 A1 * | 5/2010 | Yune | 430/5 |

FOREIGN PATENT DOCUMENTS

| | | |
|---|---|---|
| JP | 04-324618 | 11/1992 |
| KR | 1997-0054993 A | 7/1997 |
| KR | 10-2003-0026780 A | 4/2003 |

* cited by examiner

*Primary Examiner* — Amanda C. Walke

(57) ABSTRACT

A three dimensional scaffold having a three dimensional structure is easily fabricated by employing a lithography process used in a semiconductor manufacturing process. A method of fabricating the same is also disclosed have a conformational structure. In the method of fabricating a three dimensional scaffold having the conformational structure according to the present invention, a first pattern is first formed on a substrate by using a first photoresist through a lithography process, and a temporary photoresist is coated on a whole surface of the substrate. Next, a temporary pattern exposing the upper part of the first pattern to the surface is formed by using the lithography process, and a second photoresist contacting the first pattern via the temporary pattern is coated on the whole surface of the substrate. Subsequently, the temporary pattern is removed after exposing and developing the second photoresist, and then, a second pattern connected to the first pattern is formed with the second photoresist, to thereby obtain the three dimensional scaffold. Accordingly, the present invention can readily fabricate a three dimensional scaffold having a three dimensional structure through a lithography process using a photoresist.

20 Claims, 11 Drawing Sheets

THREE DIMENSIONAL SCAFFOLD AND METHOD OF FABRICATING THE SAME

This application claims priority to Korean Patent Application No. 10-2005-0077847, filed Aug. 24, 2005, and all the benefits accruing therefrom under 35 U.S.C. §119, the contents of which in its entirety are herein incorporated by reference.

BACKGROUND OF THE INVENTION

1. Field of the Invention

The present invention generally relates to a three dimensional scaffold and a method of fabricating the same, and more particularly, to a three dimensional scaffold having a three dimensional structure which can be easily fabricated through a lithography process generally used in the semiconductor manufacturing process, and a method of fabricating the same.

2. Description of the Related Art

The studies of pathology and biotechnology, such as diagnosis of disease or evaluation on the effect of medicinal therapy, have actively progressed as one of the leading future technologies. As one of the methods for accelerating such studies, a biochip has been studied and developed.

For the effective use of the biochip in biomedical engineering and related fields, however, target cells should be abundantly cultured in the biochip through a repeatedly practicable method. A three dimensional scaffold has been proposed for use as a structure for the cell culture in this manner.

FIGS. 1 to 3 are photographs of three dimensional scaffolds fabricated according to existing methods.

As illustrated in FIGS. 1 to 3, the existing three dimensional scaffolds have a conformational structure containing numerous pores on the surface thereof. Therefore, it is possible to effectively culture a large quantity of cells by using such three dimensional scaffolds, which advance the adoption of biotechnology as a kind of industrial technology.

However, since all the existing three dimensional scaffolds described in the figures have an irregular or non-uniform shape, it is very difficult to repeatedly manufacture a three dimensional scaffold having a same structure.

To overcome such a problem, U.S. Pat. No. 6,686,184 discloses a method capable of repeatedly fabricating microstructures with uniform features, which can be used in the manufacture of microfluidic systems.

However, even though this method can fabricate a repeatable microstructure through a lithography process using a photoresist in fabricating the microfluidic systems, it has a disadvantage in that the layer of each structure has to be adhered to each other after their patterns are independently formed or each layer has to be formed by adhering one layer to another layer, one by one.

Therefore, the existing methods cannot be practically applied to the fabrication of a conformational structure due to the very complicated process, thereby making it impossible to manufacture a three dimensional scaffold having a regular or uniform structure.

BRIEF SUMMARY OF THE INVENTION

Accordingly, a primary aspect or feature of the present invention is to provide a three dimensional scaffold capable of repeatedly being fabricated as a three dimensional structure having a regular conformation by employing a lithography process and a method of fabricating the same.

Another aspect or feature of the present invention is to provide a method of fabricating a three dimensional scaffold which can be readily used to mass-produce the three dimensional structure by employing a lithography process, to thereby facilitate the industrial application of genetic engineering.

Still another aspect or feature of the present invention is to offer a three dimensional scaffold having a regular conformation which is capable of enhancing homogeneity of cells cultured in the three dimensional scaffolds.

According to the method of fabricating a three dimensional scaffold having a conformational structure in an exemplary embodiment of the present invention to accomplish the above aspects or features, a first pattern is first formed on a substrate using a first photoresist through a lithography process, and a temporary photoresist is coated on a whole surface of the substrate. Next, a temporary pattern exposing an upper part of the first pattern to the surface is formed using the lithography process, and a second photoresist contacting the first pattern via the temporary pattern is coated on the whole surface of the substrate. Subsequently, the temporary pattern is removed after exposing and developing the second photoresist; and then, a second pattern connected to the first pattern is formed with the second photoresist, to thereby obtain the three dimensional scaffold.

In an exemplary embodiment of the method of the present invention, the first photoresist and second photoresist are negative type, and the temporary photoresist is positive type.

In an exemplary embodiment of the method of the present invention, the temporary pattern and first pattern are formed with the same mask.

In an exemplary embodiment of the method of the present invention, the method further comprises, after coating the second photoresist, flattening the second photoresist.

In an exemplary embodiment of the method of the present invention, the temporary pattern is removed while developing the second photoresist.

In an exemplary embodiment of the method of the present invention, a third pattern connected to the second pattern is formed by repeating the coating the temporary photoresist through the forming the second pattern after the forming the second pattern.

In an exemplary embodiment of the method of the present invention, a thickness of the temporary photoresist is thicker than that of the first pattern.

Further, the present invention is characterized by allowing a three dimensional scaffold to have a conformational structure in which a three dimensional structure is repeatedly arranged at regular intervals using a semiconductor lithography process.

The three dimensional scaffold of the present invention is characterized by repeating the three dimensional structure in a horizontal direction, and by laminating the three dimensional structure vertically.

The three dimensional scaffold of the present invention is characterized in that a material of the three dimensional structure is a photoresist.

BRIEF DESCRIPTION OF DRAWINGS

The above and other aspects and features of the present invention will become apparent from the following detailed description of exemplary embodiments taken in conjunction with the accompanying drawings, in which.

DETAILED DESCRIPTION OF THE PRESENT INVENTION

Figure 1:
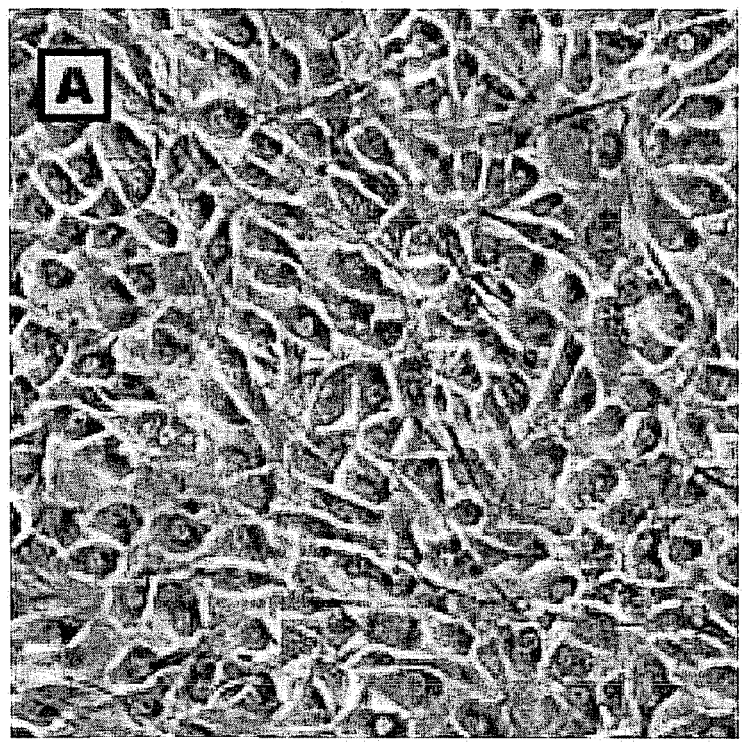
FIGS. 1 to 3 are photographs of three dimensional scaffolds fabricated according to conventional methods.
Figure 2:
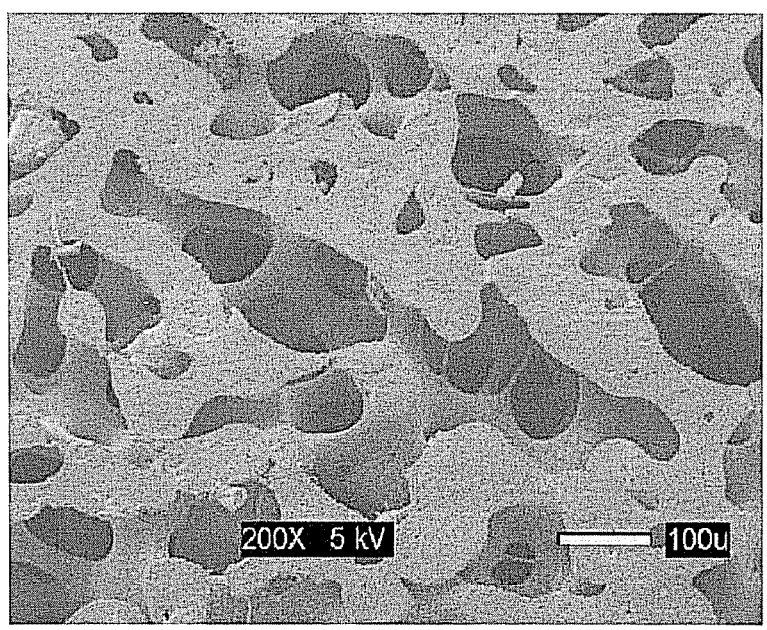
Figure 3:
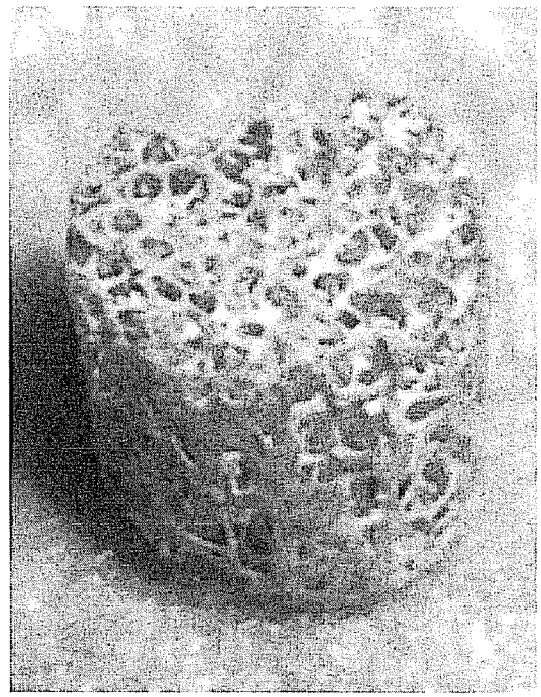

Hereinafter, exemplary embodiments of the present invention will be described in more detail with reference to the accompanying drawings, wherein identical reference numerals designate substantially identical or functionally identical elements. It will be understood in the following disclosure of the present invention, that as used herein, the term "and/or" includes any and all combinations of one or more of the associated listed items. In addition, the singular forms "a", "an" and "the" are intended to include the plural forms as well, unless the context clearly indicates otherwise. It will be further understood that the terms "comprise", "comprises", and "comprising," when used in this specification, specify the presence of stated features, integers, steps, operations, elements, components, and/or combination of the foregoing, but do not preclude the presence and/or addition of one or more other features, integers, steps, operations, elements, components, groups, and/or combination of the foregoing. The use of the terms "first", "second", and the like, where included, are for purposes of distinguishing elements only, and therefore should not be considered as implying any particular order or sequence unless otherwise specified.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIGS. 4A, 5A, 6A, 7A, 8A and 8C are plan views of three dimensional scaffolds fabricated stepwise according to an exemplary embodiment of a method of fabricating a three dimensional scaffold according to the present invention. FIGS. 4B, 5B, 6B, 7B, 8B and 8D are partial cross-sectional views of three dimensional scaffolds that are obtained by cutting along line of A-B in FIGS. 4A, 5A, 6A, 7A, 8A and 8C, respectively.

As described in FIGS. 4A to 8B, a first photoresist is coated on a surface of a substrate 100, and a first pattern 110 is formed with the first photoresist by using a lithography process according to the method of fabricating a three dimensional scaffold of the present invention. The substrate 100 functions as a frame supporting a structure of the three dimensional scaffold, some examples of which include a silicone substrate, a glass substrate, a quartz substrate, a Teflon substrate and the like.

Figure 4A:
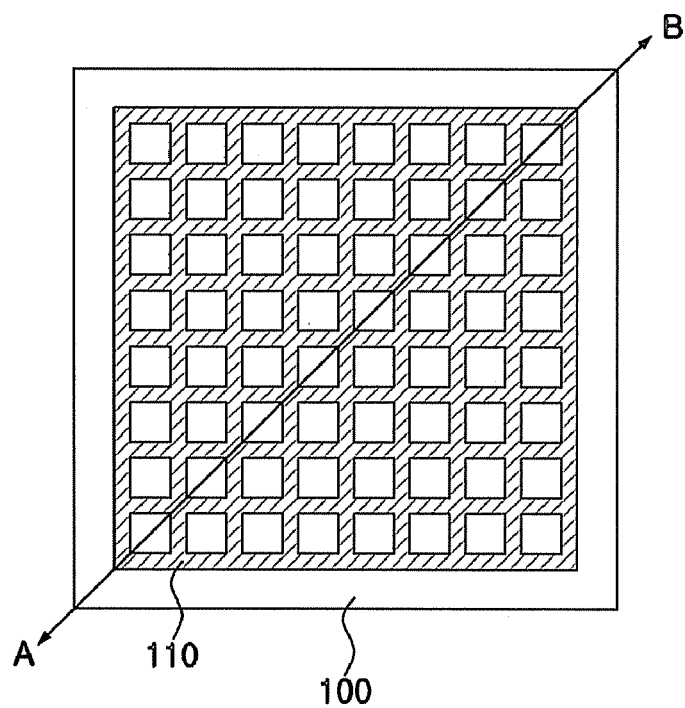
FIGS. 4A, 5A, 6A, 7A, 8A and 8C are plan views of three dimensional scaffolds fabricated stepwise according to an exemplary embodiment of a method of fabricating a three dimensional scaffold according to the present invention.
Figure 4B:
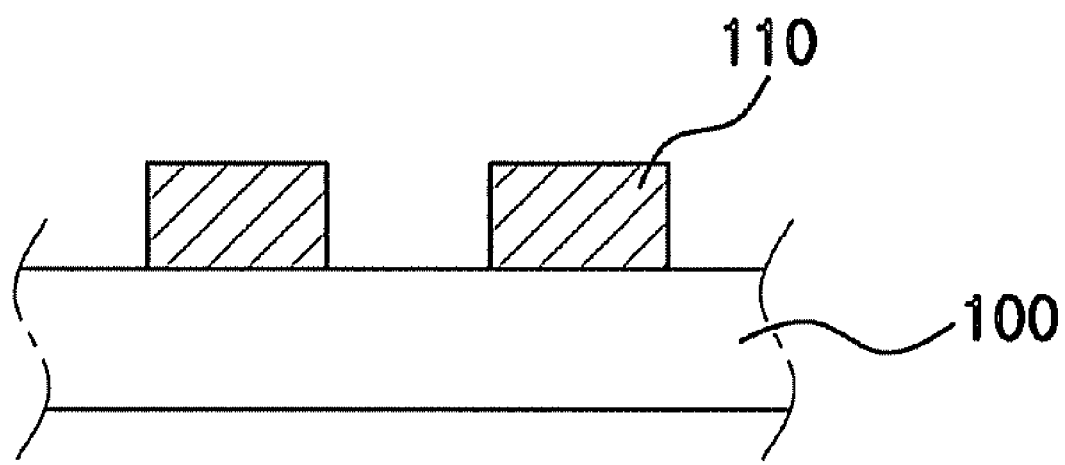
FIGS. 4B, 5B, 6B, 7B, 8B and 8D are partial cross-sectional views of three dimensional scaffolds that are obtained by cutting along line of A-B in the plan views of FIGS. 4A, 5A, 6A, 7A, 8A and 8C, respectively.
Figure 5A:
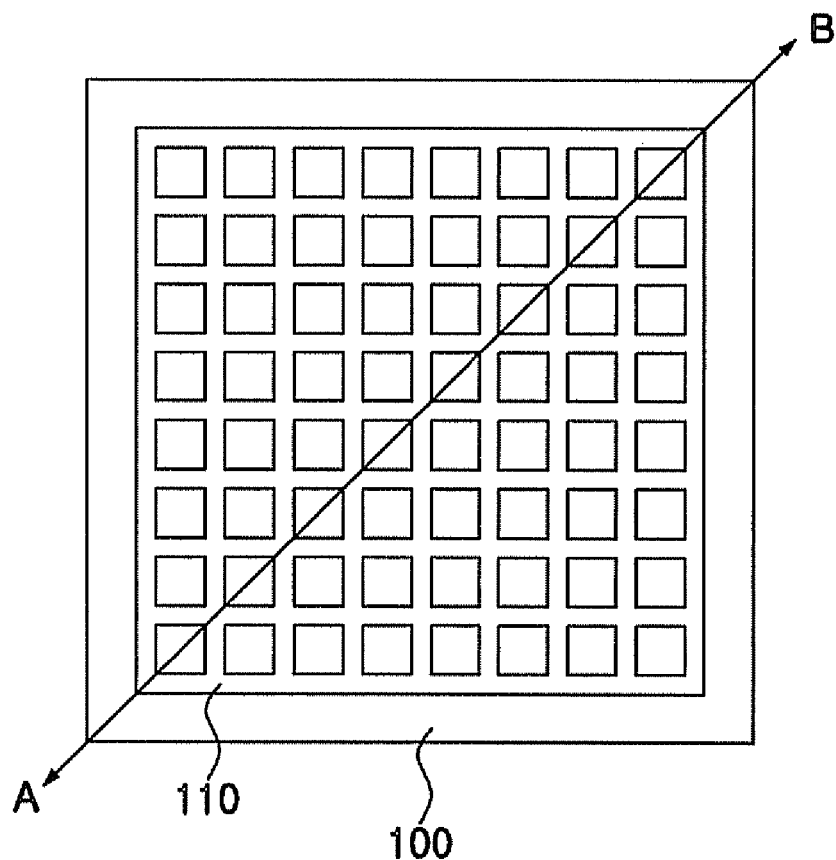
Figure 5B:
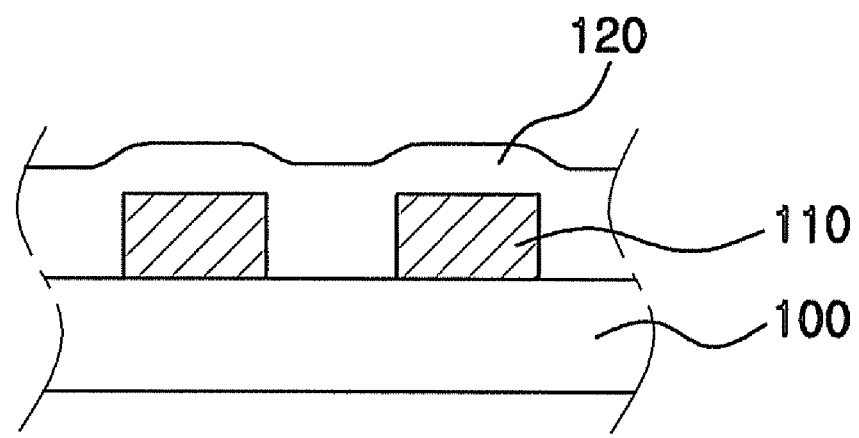
Figure 6A:
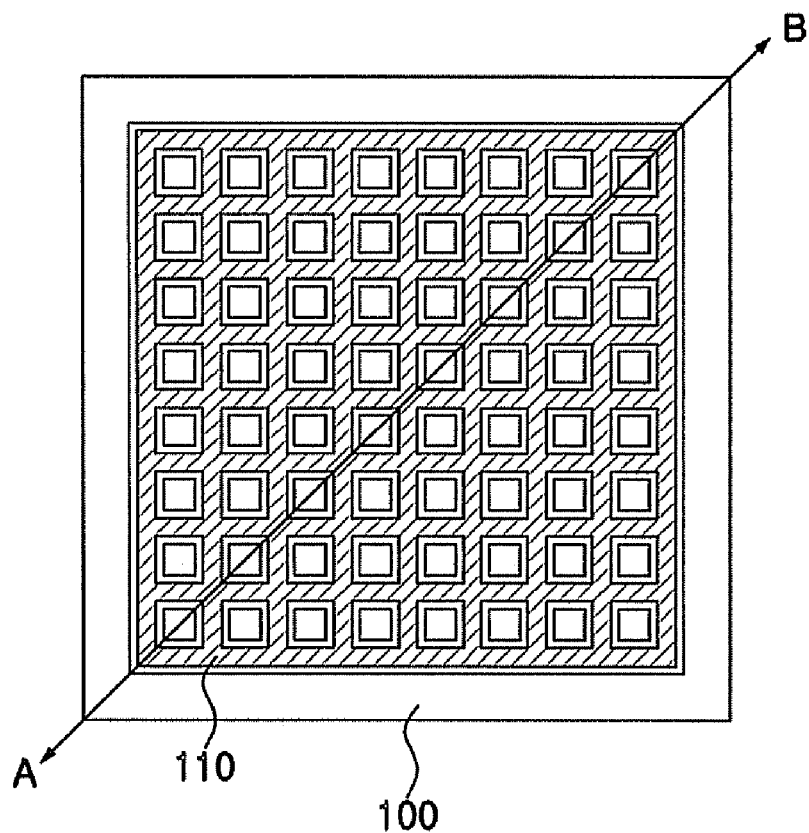
Figure 6B:
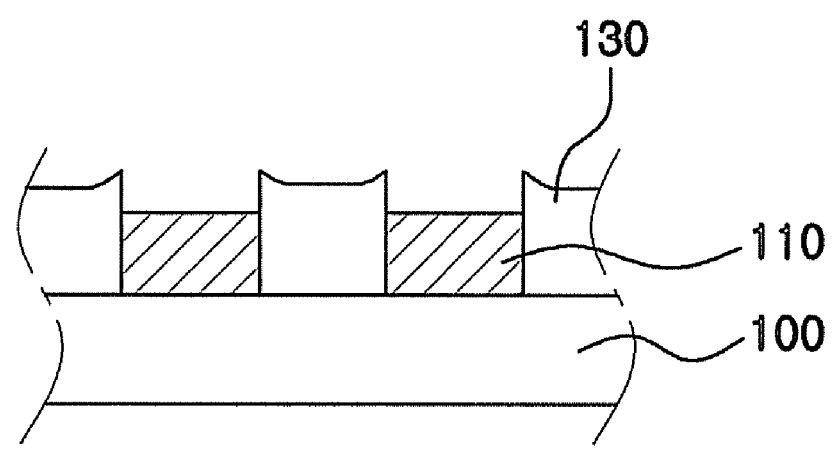

For example, the first pattern 110 is formed in a lattice pattern, as illustrated in FIG. 4A, by employing a negative photoresist so that it can be used as a structure of the three dimensional scaffold. The negative photoresist used therein contains epoxy as a main ingredient which shows high surface adhesive strength and chemical resistance. In exemplary embodiments, it is preferable to apply SU-8 commercially available from MicroChem Corp.

Since the negative photoresist to be formed as an opposite pattern to a chrome pattern of a mask (not shown) exhibits superior hardness and chemical resistance than a positive photoresist. The negative photoresist is more suitable for employment as a structure of the three dimensional scaffold than the positive photoresist.

As shown in FIGS. 5A to 6B, a temporary photoresist 120 is coated on the whole surface of the substrate 100, and a temporary pattern 130 exposing the upper part of the first pattern 110 to the surface is formed by using the lithography process. The temporary photoresist can be easily formed by using a positive photoresist, and the temporary pattern 130 is formed by applying the mask used in the first pattern 110 to the positive photoresist.

To facilitate the following flattening and lithography process steps, it is preferable to coat the temporary photoresist 120 to be thicker than the thickness of the first pattern 110.

At this time, since the temporary pattern 130 has to be removed in the following step, care should be taken to ensure that the temporary pattern 130 is not excessively hardened by heat treatment.

Figure 7A:
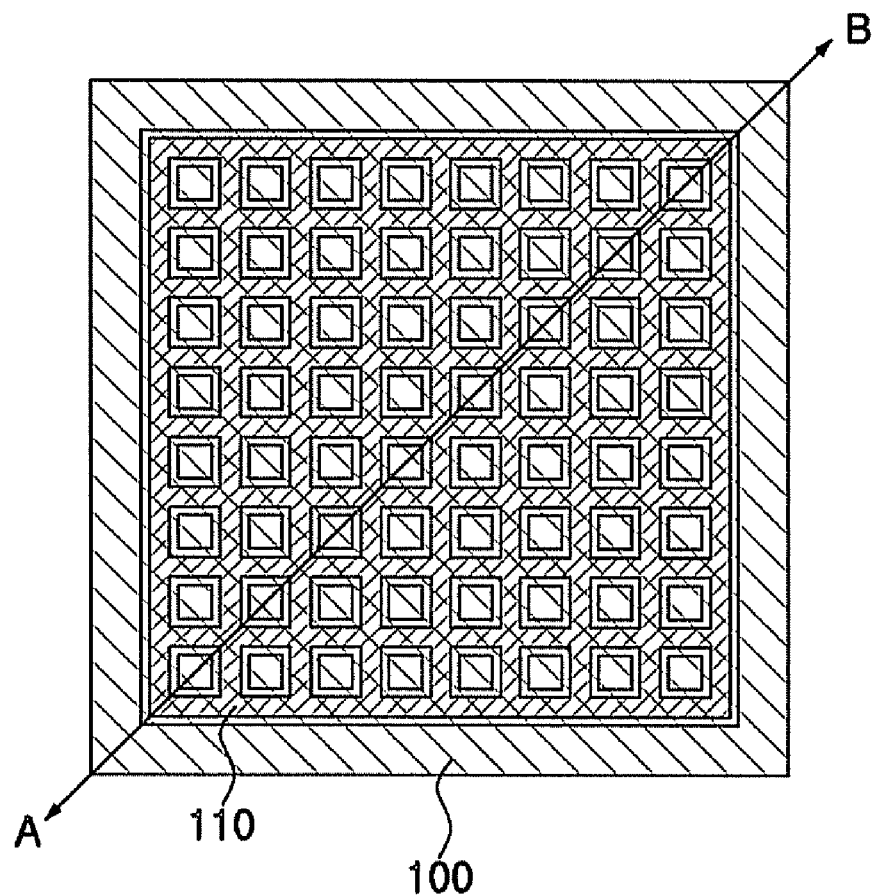
Figure 7B:
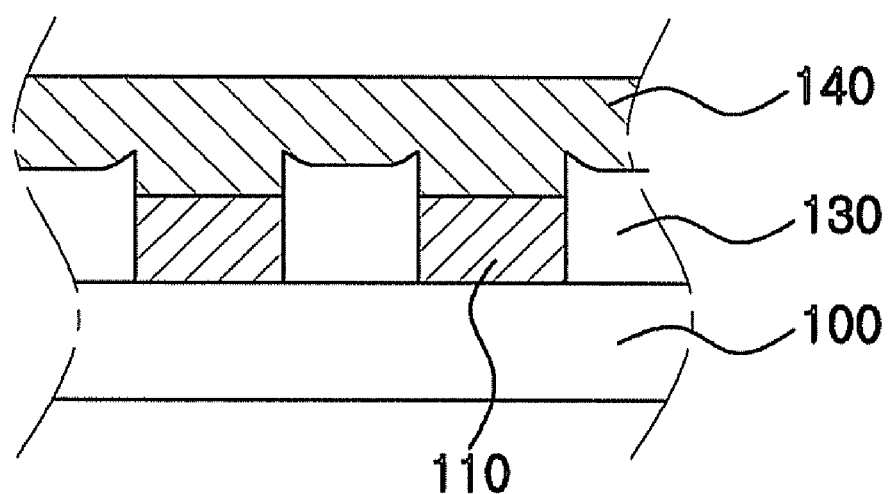

As described in FIGS. 7A and 7B, a second photoresist 140 contacting the first pattern 110 via the temporary pattern 130 is coated on the whole surface of the substrate 100. In an exemplary embodiment of the present invention, it is possible to increase adhesive strength between the first pattern 110 and the second photoresist 140 and also simplify the fabrication process, by applying the same photoresist as the first photoresist for the second photoresist.

In order to continuously laminate numerous structures of the three dimensional scaffold, it is preferable to flatten the second photoresist 140 through heat treatment. The flattening of photoresist by heat treatment is based on the characteristic that the photoresist flows when applying an appropriate temperature thereto, and the temperature for flattening is determined according to the type of photoresist used.

Figure 8A:
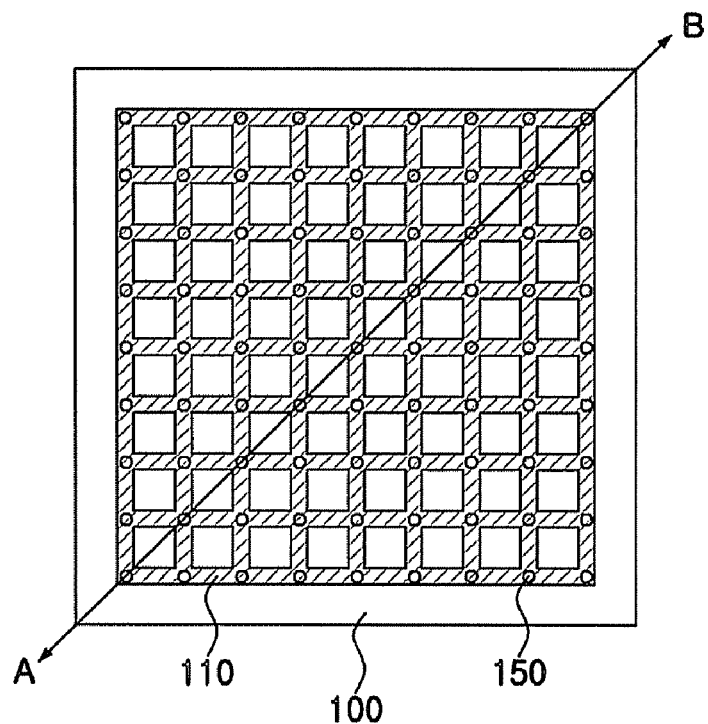
Figure 8B:
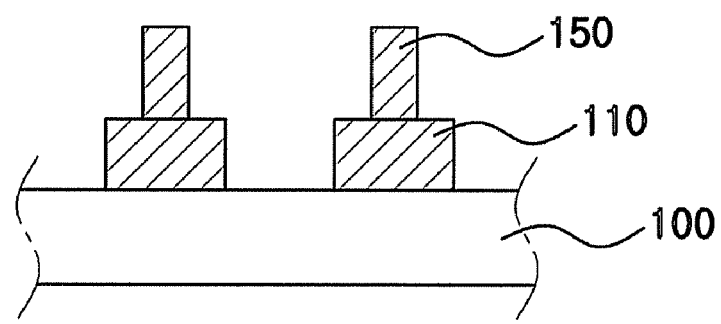

As shown in FIGS. 8A and 8B, a second pattern 150 sterically connected to the first pattern 110 in part is formed by developing the exposed second photoresist 140 using a mask required for the structure of a three dimensional scaffold, and the temporary pattern 130 located at the lower part of the second photoresist 140 is removed.

At this time, since the temporary pattern 130 is formed with the positive photoresist, it can be easily removed by using chemicals, which develop a negative photoresist such as SU-8, thus removing the temporary pattern 130 without any further steps.

Figure 8C:
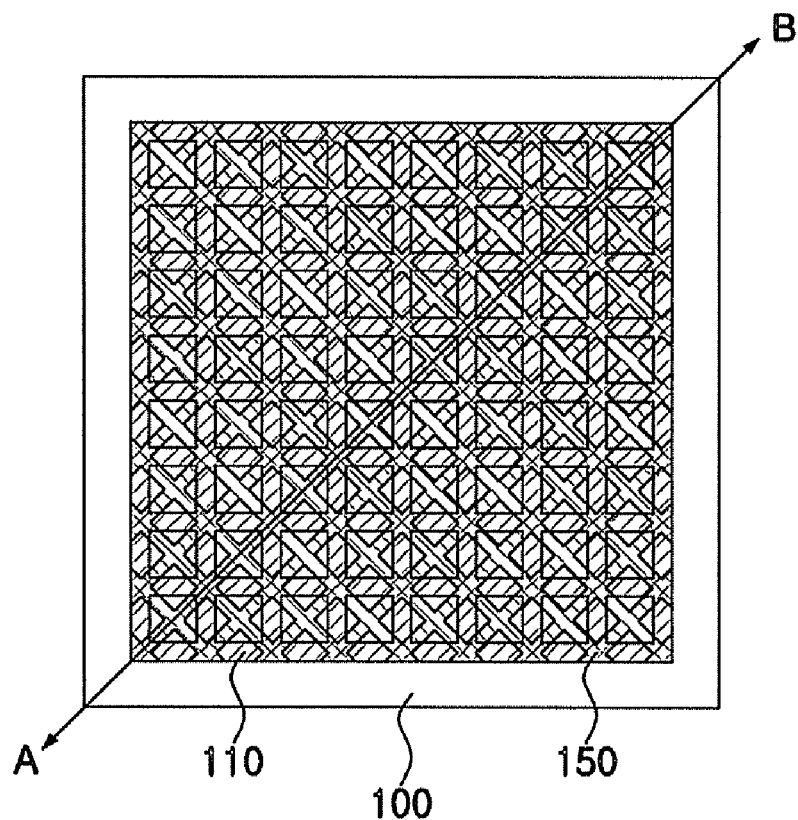
Figure 8D:
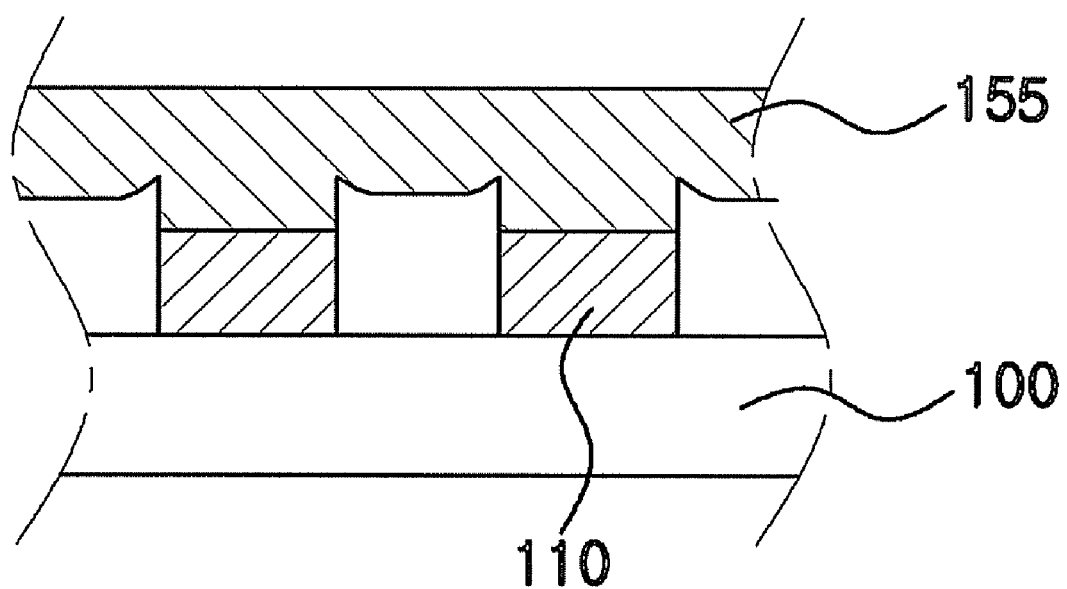

As presented in FIGS. 8C and 8D, another second pattern 155 sterically connected to the first pattern 110 in part is formed by developing the exposed second photoresist 140 using a mask required for the structure of a three dimensional scaffold having a different structure from FIG. 8A, and the temporary pattern 130 located at the lower part of the second photoresist 140 is removed according to the same method as described in FIG. 8B.

As illustrated in FIG. 8D, the another second pattern 155, which is formed with the part extending up to where the first pattern 110 as a lower pattern is not formed, can be easily formed by an exemplary embodiment of a method of fabricating a three dimensional scaffold according to the present invention.

In a case of laminating other structures in succession following the formation of the second pattern 150, it is possible to continuously fabricate a conformational structure by repeating the process from the coating the temporary photoresist 120 to the process of forming the second pattern 150.

Figure 9:
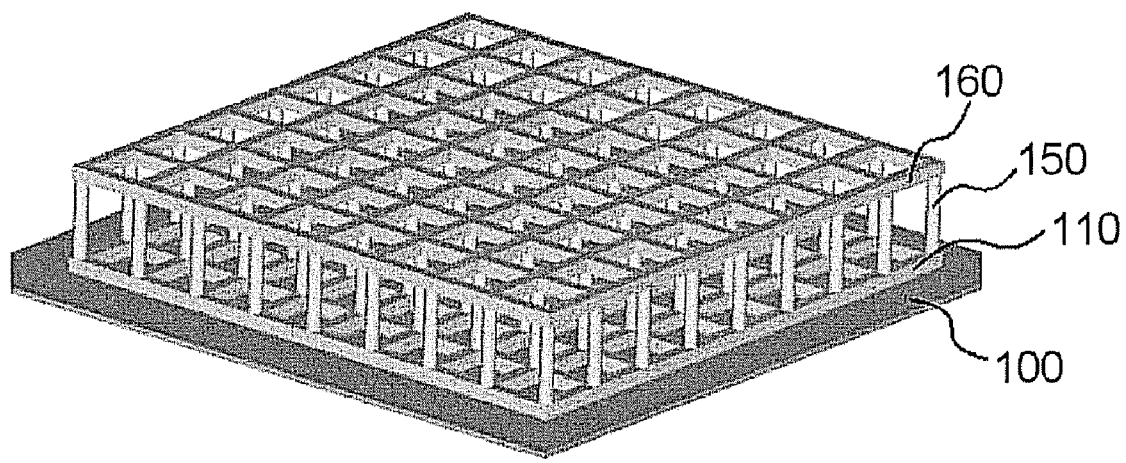
FIG. 9 is a perspective view of the three dimensional scaffold fabricated up to a third pattern according to the exemplary embodiment of the method of fabricating a three dimensional scaffold according to the present invention.
Figure 10:
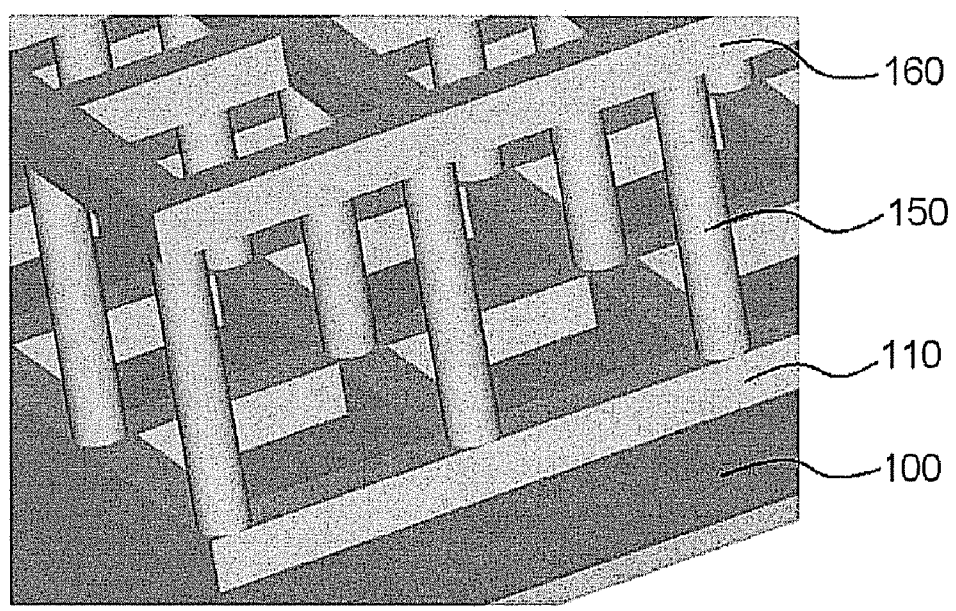
FIG. 10 is a partial enlarged view of FIG. 9.

FIG. 9 is a perspective view of the three dimensional scaffold fabricated up to a third pattern according to an exemplary method of fabricating a three dimensional scaffold according to the present invention. FIG. 10 is a partial enlarged view of FIG. 9.

Referring to FIGS. 9 and 10, a third pattern 160 is formed by conducting the process of coating the temporary photoresist 120 to the forming the second pattern 150 using the same mask as employed in the formation of the first pattern 110.

At this time, if the first pattern 110, the second pattern 150 and the third pattern 160 employ the same photoresist, it is possible to fabricate a three dimensional scaffold having the structure laminated with a single photoresist, which simplifies the fabrication process. Another advantage is that an adhesive strength among the first pattern 110, the second pattern 150 and the third pattern 160 can be increased due to the use of the same photoresist.

Unlike the existing methods, the exemplary method of the present invention fabricates a three dimensional scaffold by employing the lithography process; and thus, the three dimensional scaffold thus fabricated has three dimensional structures that are repeatedly arranged at regular intervals.

The three dimensional structures of the present invention as described above are repeated in the horizontal direction and various types of such three dimensional structures are vertically laminated. Further, materials available in the fabrication of the three dimensional structures may include several types of materials conventionally used in semiconductor manufacturing processes. However, since such three dimensional scaffolds can be easily fabricated using merely the lithography process, it is preferable to utilize a photoresist.

Figure 11:
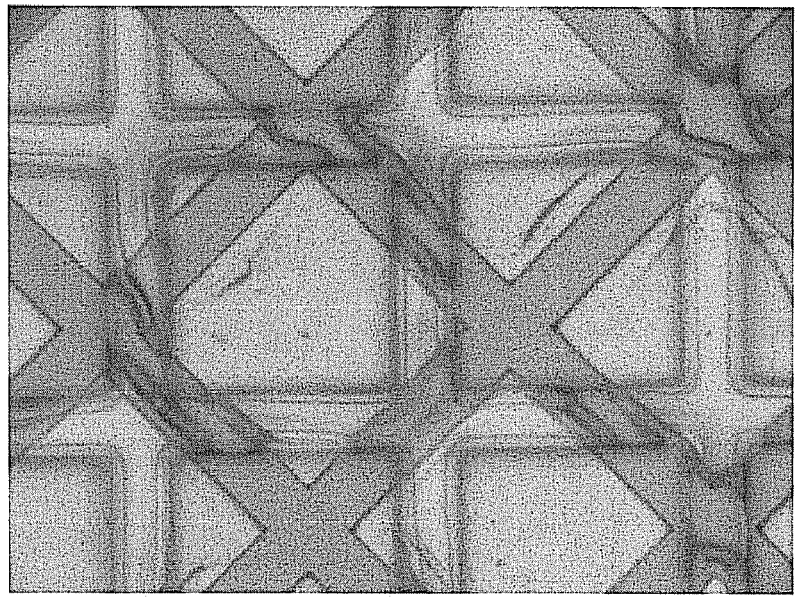
FIG. 11 is a photograph of a plan view of the three dimensional scaffold fabricated in accordance with an exemplary embodiment of the present invention.
Figure 12:
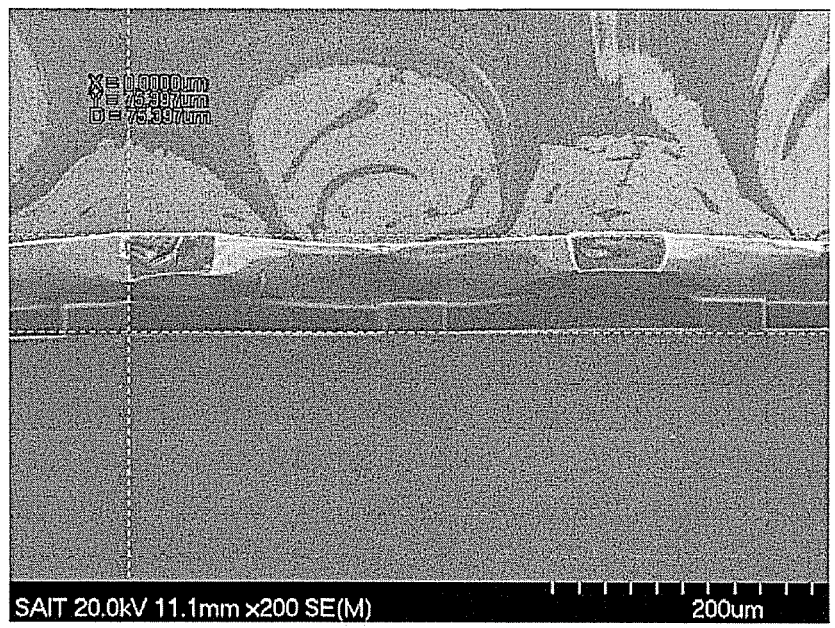
FIGS. 12 and 13 are photographs of a cross-sectional view and perspective view of FIG. 11, respectively.
Figure 13:
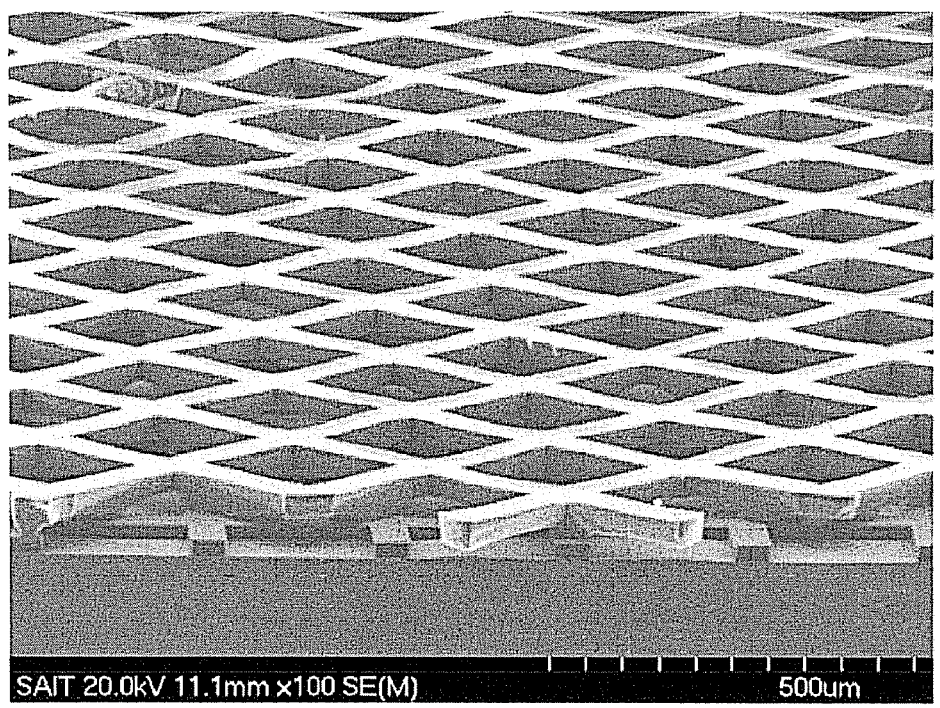

FIG. 11 is a photograph of a plan view of the three dimensional scaffold fabricated in accordance with an exemplary embodiment of the present invention. FIGS. 12 and 13 are photographs of a cross-sectional view and a perspective view of FIG. 11, respectively.

In an exemplary embodiment of the present invention, the photoresist and substrate used in the fabrication of the three dimensional scaffold of FIG. 11 are SU-8 and a silicone substrate, respectively. For the photoresist pattern, for example, a mask of mesh pattern is employed.

The thickness of the photoresist of the first pattern is 25 μm, and that of the third pattern is 35 μm. As illustrated in FIG. 13, the first pattern binds to the second pattern at a portion where the first pattern overlaps the second pattern, thereby obtaining firm adhesion therebetween.

The exemplary embodiments of the three dimensional scaffold in accordance with the present invention can be applied to other embodiments, for example, a filter capable of classifying cells according to size.

Figure 14:
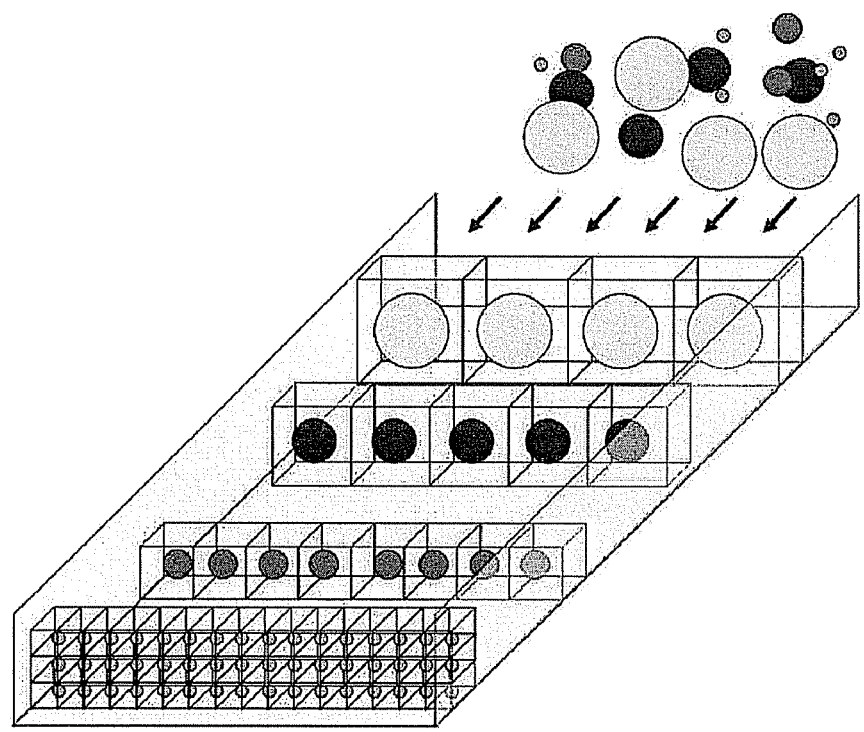
FIG. 14 is a perspective view of a filter fabricated in accordance with an exemplary embodiment of the present invention.

FIG. 14 is a perspective view of an exemplary embodiment of a filter fabricated in accordance with an exemplary embodiment of the present invention.

As depicted in FIG. 14, the three dimensional scaffold of the present invention can be employed to classify diverse types of cells having different sizes according to size.

In a case of moving the cells in a direction indicated by arrows in FIG. 14, the cells can be efficiently classified according to size by a filter whose opening becomes gradually smaller. It is preferable to fabricate the three dimensional scaffold having such a structure in a vertical direction or a horizontal direction in accordance with exemplary embodiments of a method of fabricating the three dimensional scaffold of the present invention.

As mentioned above, the present invention can readily fabricate a three dimensional scaffold having a three dimensional structure through a lithography process using a photoresist.

In addition, the present invention can fabricate a three dimensional scaffold having a regular conformation, differently from existing conventional three dimensional scaffolds, to allow its mass-production by using a lithography process; and accordingly, it is suitable for industrial application in genetic engineering.

Moreover, since the three dimensional scaffold has a regular structure fabricated according to exemplary embodiments of a method of the present invention, it can provide high homogeneity in conducting cell culture using such a method.

While the present invention has been shown and described with respect to particular exemplary embodiments, it will be apparent to those skilled in the art that many changes and modifications may be made without departing from the spirit and scope of the present invention as defined in the appended claims.

What is claimed is:

1. A method of fabricating a three dimensional scaffold having a conformational structure, the method comprising:
    forming a first pattern on a substrate with a first photoresist by using a lithography process;
    coating a temporary photoresist on a whole surface of the substrate;
    forming a temporary pattern exposing the upper part of the first pattern to the surface by using the lithography process;
    coating a second photoresist contacting the first pattern via the temporary pattern on the whole surface of the substrate;
    exposing the second photoresist; and
    developing the second photoresist and removing the temporary pattern to thereby form a second pattern connected to the first pattern with the second photoresist.

2. The method according to claim 1, wherein the first photoresist and second photoresist are negative type, and the temporary photoresist is positive type.

3. The method according to claim 1, wherein the temporary pattern and first pattern are formed with a same mask.

4. The method according to claim 3, wherein the first photoresist and second photoresist are negative type, and the temporary photoresist is positive type.

5. The method according to claim 1, further comprising flattening the second photoresist, after the coating the second photoresist.

6. The method according to claim 5, wherein the first photoresist and second photoresist are negative type, and the temporary photoresist is positive type.

7. The method according to claim 1, wherein the temporary pattern is removed while developing the second photoresist.

8. The method according to claim 7, wherein the first photoresist and second photoresist are negative type, and the temporary photoresist is positive type.

9. The method according to claim 1, wherein a third pattern connected to the second pattern is formed after the developing the second photoresist and the removing the temporary pattern by repeatedly conducting the forming the temporary pattern, the coating the second photoresist, the exposing the second photoresist, and the developing the second photoresist and the removing the temporary pattern.

10. The method according to claim 9, wherein the first photoresist and second photoresist are negative type, and the temporary photoresist is positive type.

11. The method according to claim 1, wherein a thickness of the temporary photoresist is thicker than that of the first pattern.

12. The method according to claim 1, wherein the first photoresist and second photoresist are negative type, and the temporary photoresist is positive type.

13. A three dimensional cell culture scaffold comprising:
(a) a substrate; and
(b) a three dimensional structure, wherein the three dimensional structure comprises a first pattern comprising a first photoresist on the substrate, and a second pattern comprising a second photoresist connected to the first pattern, and wherein the first and second photoresists can be the same or different.

14. The three dimensional scaffold according to claim 13, wherein the three dimensional structure consists of one or more photoresist materials.

15. The three dimensional scaffold according to claim 13, wherein the scaffold comprises a three dimensional structure repeatedly arranged at regular intervals.

16. The three dimensional scaffold according to claim 15, wherein the three dimensional structure is repeated in a horizontal direction.

17. The three dimensional scaffold according to claim 15, wherein the three dimensional structure is laminated vertically.

18. The three dimensional scaffold according to claim 13, wherein the scaffold comprises a structure capable of classifying cells according to size.

19. The three dimensional scaffold according to claim 16, wherein the scaffold comprises openings that become smaller in a vertical or horizontal direction.

20. The three dimensional scaffold according to claim 13, wherein the first and second photoresists are negative photoresists.

* * * * *